United States Patent [19]
Winter et al.

[11] Patent Number: 5,624,821
[45] Date of Patent: Apr. 29, 1997

[54] ANTIBODIES WITH ALTERED EFFECTOR FUNCTIONS

[75] Inventors: Gregory P. Winter, Cambridge; Alexander R. Duncan, Wimbledon; Dennis R. Burton, Sheffield, all of Great Britain

[73] Assignee: Scotgen Biopharmaceuticals Incorporated, Menlo Park, Calif.

[21] Appl. No.: 479,752

[22] Filed: Jun. 7, 1995

Related U.S. Application Data

[63] Continuation of Ser. No. 208,084, Mar. 9, 1994, which is a continuation of Ser. No. 814,035, Dec. 24, 1991, abandoned, which is a continuation of Ser. No. 303,668, Jan. 18, 1989, abandoned.

[30] Foreign Application Priority Data

| | | | |
|---|---|---|---|
| Mar. 18, 1987 | [GB] | United Kingdom | 8706425 |
| Aug. 10, 1987 | [GB] | United Kingdom | 8718897 |
| Dec. 1, 1987 | [GB] | United Kingdom | 8728042 |
| Mar. 18, 1988 | [WO] | WIPO | PCT/GB88/00211 |

[51] Int. Cl.$^6$ .................... C12N 15/00; C12N 1/20; A61K 39/395
[52] U.S. Cl. .................. 435/69.6; 435/172.3; 435/252.3; 424/133.1; 530/387.3
[58] Field of Search ................. 530/387.3; 424/133.1; 435/69.6, 172.3, 252.3

[56] References Cited

FOREIGN PATENT DOCUMENTS 0125023  11/1984  European Pat. Off. .

OTHER PUBLICATIONS

Emanuel et al "Chemical Verification of the C1q Receptor Site on IgG", FEBS Letters, vol. 137, No. 2, 1982, pp. 298–302.

Rosenberg et al., "Synthesis in yeast of a functional oxidation-resistant mutant of human $\alpha_1$-antritrypsin", Nature, vol. 312, 1984, pp. 77–80.

Jallat et al, "Antiprotease targeting: altered specificity of $\alpha_1$-antitrypsin by amino acid replacement at the reactive centre", Blood Transfusion and Immunobacmatology, vol. 29, No. 4, 1986, pp. 287–298.

Allen, R et al., "Studies on the Complement–Binding Site of Rabbit Immunoglobulin G–I. Modification of Tryptophan Residues and their Role in Anticomplementary Activity of Rabbit IgG", *Immunochemistry*, 11: 175–180 (1974).

Burton, "Immunoglobulin G. Functional Sites", *Molecular Immunology*, vol. 22, No. 3, pp. 161–206 (1985).

Burgess et al., "Possible Dissociation of the Heparin–binding and Mitogenic Activities of Heparin–binding (Acidic Fibroblast) Growth Factor–1 from its Receptor–binding Activities by Site–directed Mutagenesis of a Single Lysine Residue", *Journal of Cell Biology*, 111: 2129–2138 (1990).

Clackson, T. et al., "Sticky Feel–Directed Mutagenesis And Its Application To Swapping Antibody Domains", *Nucleic Acids Research*, vol. 17, No. 24, pp. 10163–10170 (1989).

Dalbaldie–McFarland et al., "Oligonucleotide–directed Mutagenesis as a General and Powerful Method for Studies of Protein Function", *Proc. Nat. Sci. Acad.* (USA), vol. 79, pp. 6409–6313, Nov., 1982.

Duncan et al., "Localization of the Binding Site for the Human High Affinity Fc Receptor on IgG", *Nature* vol. 332, pp. 563–564, 7 Apr. 1988.

(List continued on next page.)

*Primary Examiner*—Lia Feisee
*Assistant Examiner*—Julie E. Reeves
*Attorney, Agent, or Firm*—Spencer & Frank

[57] ABSTRACT

An antibody with an altered function, e.g. altered affinity for an effector ligand such as Fc receptor (FcR) on a cell or the C1 component of complement is produced by replacing at least one amino acid residue in the constant portion of the antibody with a different residue.

25 Claims, 8 Drawing Sheets

OTHER PUBLICATIONS

Hofstaetter et al., "S–sulfonation: A Reversible Chemical Modification of Human Immunoglobulins Permitting Intravenous Application. II. Effect on Fc Mediated Effector Functions", *Chemical Abstracts*, vol. 99, No. 11, pp. 423, 12 Sep. 1983, and Vox Sang, 45: 155–165 (1983).

Ingram, "Gene Mutations in Human Haemoglobin: The Chemical Difference Between Normal and Sickle Cell Haemoglobin", *Nature* 180: 326–28 (1957).

Lazar et al., "Transforming Growth Factor α: Mutation of Aspartic Acid 47 and Leucine 48 Results in Different Biological Activities", *Molecular and Cellular Bioilogy*, vol. 8, No. 3, pp. 1247–1252 (1988).

Leatherbarrow et al., "Effector Functions of a Monoclonal Aglycosylated Mouse IgG2a: Binding and Activation of Complement C1 and Interaction with Human Monocyte Fc Receptor", *Molecular Immunology*, vol. 22, No. 4, pp. 407–415 (1985).

Liu et al., Production of a Mouse–Human Chimeric Monoclonal Antibody to CD20 with Potent Fc–Dependent Biologic Activity, *J. Immunol.* 139: 3521–26 (1987).

Lund et al., "Human FcγRI and Fc RII Interact with Distinct But Overlapping Sites on Human IgG", *J. Immunol.*, vol. 147, No. 8, pp. 2657–2662 (1991).

Morrison, "Transfectomas Provide Novel Chimeric Antibodies", *Science* 229: 1202–1207 (1985).

Morrison et al., "Chimeric Human Antibody Molecules: Mouse Antigen–binding Domains with Human Constant Region Domains", *Proc. Natl. Acad. Sci.* (USA) 81: 6851–6855 Nov. 1984.

Nose et al., "Biological Significance of Carbohydrate Chains on Monoclonal Antibodies", *Proc. Natl. Acad. Sci.* (USA) 80: 6632–6636 (1983).

Partridge et al., *Molecular Immunology*, vol. 23, No. 12, pp. 1365 (1986).

Pollack et al., "Identification of Mutant Monoclonal Antibodies with Increased Antigen Binding", *Proc. Natl. Acad. Sci.* (USA) 85: 2298–2302 (1988).

Sandlie et al., "Engineering Monoclonal Antibodies to Determine the Structural Requirements for Complement Activation and Complement Mediated Lysis", *Molecular Immunology*, vol. 28, No. 12, pp. 1361–1368 (1991).

Sharon et al., "Site–Directed Mutagenesis of an Invariant Amino Acid Residue at the Variable–Diversity Segments Junction of an Antibody", *Proc. Natl. Acad. Sci.* (USA) 83: 2628–31 (1986).

Shin et al., "Genetically–Engineered Antibodies: Tools for the Study of Diverse Properties of the Antibody Molecule", *Immunological Reviews*, No. 130, pp. 87–92. (1992).

Stanfield et al., "Antigen–induced Conformational Changes in Antibodies: A Problem for Structural Prediction and Design", *Tib Tech*, vol. 12, pp. 275, Jul. 1994.

Tao et al., "Studies of Aglycosylated Chimeric Mouse–Human IgG", *Journal of Immunology*, 143: 2595–2601 (1989).

Vivanco–Martinez et al., "Chemical Modification of Carboxyl Groups in Human Fc Fragment: Structural Role and Effect on the Complement Fixation", *Chemical Abstracts*, vol. 93, No. 7, pp. 703, 18 Aug. 1980.

Winter et al., "Restructuring Enzymes and Antibodies, in Investigating and Exploitation of Antibody Combining Sites", Reid et al., ed., Plenum Press, 139 (1985).

Woof, J. M. et al., "Localization of The Monocyte–Binding Region On Human Immunoglobulin G", *Molecular Immunology*, vol. 23, No. 3, pp. 319–330 (1986).

Zoller et al., "Oligonucletide–directed Mutagenesis Using M13–Derived Vectors: An Efficient and General Procedure for the Production of Point Mutations in any Fragment of DNA", *Nucleic Acids Research*, vol. 10, pp. 6487–6500 (1982).

```
AACATGGAAAAATTAAGTCACAGTGCAAGCTCTGGAGGCGGAAATTTCTGACACTGCTTGCCTCAGATCAATTGTAGAAGACACGGTTCTAAGACAAAGCTAAGAACAGAATCTCC
         10        20        30        40        50        60        70        80        90       100       110       120

CH1 domain
                                                                             A  K  T  P  P  S  V  Y  P  L  A  P  G  C  G  D  T  T  G  S  S  V
AAATATCCGAGGCCACTGATAAGAAAAAGCTCACACATTTCCCTCTCTTGCAGCAGTCACTGAAGCCCCATCAGTCTATCCACTGGCCCCTGGTGTGGAGATACAACTGGTTCCTCCGT
        130       140       150       160       170       180       190       200       210       220       230       240

T  L  G  C  L  V  K  G  Y  F  P  E  S  V  T  V  T  W  N  S  G  S  L  S  S  S  V  H  T  F  P  A  L  L  Q  S  G  L  Y  T
GACTCTGGGATGCCTGGTCAAGGGCTACTTCCCTGAGTCAGTGACTGTGACTTGGAACTCTGGATCCCTGTCCAGCAGTGTGCACACCTTCCCAGCTCTCCTGCAGTCTGGACTCTACAC
        250       260       270       280       290       300       310       320       330       340       350       360

M  S  S  S  V  T  V  P  S  S  T  W  P  S  Q  T  V  T  C  S  V  A  H  P  A  S  S  T  T  V  D  K  K  L
TATGAGCAGTTCAGTGACTGTCCCCTCCAGCACTTGGCCAAGTCAGACCGTTGCTCACCTGTCCTGCAGCAGCAGCACCACGGTGGACAAAAAACTTGGTGAGAGGACATTCAG
        370       380       390       400       410       420       430       440       450       460       470       480

GGGAGAGGGATTCACCAGAGTTGAGGCAAAGTATTAGCCTATCTAAACCAGCTGGGATCCATCACCAAGGAGGTGACCTTAGCCCAGGAAGAGGGAGATACTGTCTGCCT
        490       500       510       520       530       540       550       560       570       580       590       600

CCCTCCTGGGAACATCTAGCTATGACCACTTCAAGGACATGTTCCTCTGGGATAGGTGTGCTTGTCATTTCCAGGATCATCCTGAACTAAGCCCATACCAGGACAAACTTTCCT
        610       620       630       640       650       660       670       680       690       700       710       720 hinge
                                         E  P  S  G  P  I  S  T  I  N  P  C  P  P  C  K  E  C  H  K  C
CTCTCTGGTTTGGTGCTTCTCTCCTTCAAAAAACCAGTAACATCCAGTTCAACATCAACCCCTGTCCCATGCAAGGAGTGTCACAAAT
        730       740       750       760       770       780       790       800       810       820       830       840

Sac I                                                                                                             CH2 domain
     P           A  P  N
GCCCAGTAAGTCACTACCAGAGCTGACTCCCAGGAGAATGGTAAGTGCTGTAAAAATCCCTGTAATGGAGGATAAGCCATGTACAAATCCATTTCCATCTCTCCTCATCAGCTCCTAA
        850       860       870       880       890       900       910       920       930       940       950       960

L  E  G  G  P  S  V  F  I  F  P  P  N  I  K  D  V  L  M  I  S  L  T  P  K  V  T  C  V  V  V  D  V  S  E  D  D  P  D  V
CCTCGAGGGTGGACCATCCGTCTTCATCTTCCCTCCAAATATCAAGGATGTACTCATGATCTCCCTGACACCCAAGGTCACGTGTGTGGTGGTGGATGTGAGCGAGGATGACCCAGACGT  3' GGATT
        970       980       990      1000      1010      1020      1030      1040      1050      1060      1070      1080
GGAGGACCCACCTGG     oligo EL235
  **
```

Fig. 3A

```
         Q  I  S  D  Q  L  V  T  G  E  N  V  F  V  T  A  Q  T  H  R  E  D  Y  N  S  T  I  R  V  V  S  T  L  P  I  Q  H  Q  D  W
         CCAGATCAGCTGGTTTGTGAACAACGTGGAAGTACACACAGCTCAGACAGACACAAACCCATAGAGAGGATTACAACAGTACTATCCGGGGTGGTCAGCACCCTCCCCATCCAGCACCAGGACTG
         1090      1100      1110      1120      1130      1140      1150      1160      1170      1180      1190      1200

M  S  G  K  E  F  K  C  K  V  N  N  K  D  L  P  S  P  I  E  R  T  I  S  K  I  K
         GATGAGTGGCAAGGAGTTCAAATGCAAGGTCAACAACAAGGACCTCCCATCCCCAGAGAACCATCTCAAAAATTAAAGGTGGGACCTGCAGGACAACTGCATGGGGGCTGGGATG
         1210      1220      1230      1240      1250      1260      1270      1280      1290      1300      1310      1320

CH3 domain SacI (removed)
                                                        G  L  V  R  A  P  Q  V  Y  I  L  P  P  P  A  E
         GGCATAAGAGAATAAATGTCTATGTGACAGCCTTCCACTTCAGCCATGACCTCTATGTGTTCTAACCCCACAGGGCTAGTCA[GAGCTC]ACAAGTATACATCTTGCCGCCACCAGCAG
         1330      1340      1350      1360      1370      1380      1390      1400      1410      1420      1430      1440

Q  L  S  R  K  D  V  S  L  T  C  L  V  V  G  F  N  P  G  D  I  S  V  E  W  T  S  N  G  H  T  E  E  N  Y  K  D  T  A  P
         AGCAGTTGTCCAGGAAAGATGTCAGTCTCACTTGCCTGGTCGTGGGCTTCAACCCTGGAGACATCAGTGTGGAGTGGACCAGCAATGGGCATACAGAGGAGAACTACAAGGACACCGCCAC
         1450      1460      1470      1480      1490      1500      1510      1520      1530      1540      1550      1560

V  L  D  S  D  G  S  Y  F  I  Y  S  K  L  N  M  K  T  S  K  W  E  K  T  D  S  F  S  C  N  V  R  H  E  G  L  K  N  Y  Y
         CGTGCTTGACAGTGACGGGTCTTACTTCATATATAGCAAGCTCAATATGAAAACAAGCTCTCAGTCCTTCATGCAACGTGAGACACGGAGGGTCTGAAAAATTACT
         1570      1580      1590      1600      1610      1620      1630      1640      1650      1660      1670      1680

SacI
         L  K  K  T  I  S  R  S  P  G  K  *
         ACCTGAAGAAGACCATCTCCCGGTCTCCGGGTAAAT[GAGCTC]AGCACCCCACAAAGCTCTCAGTCCTAAGAGAGACACCCACTGCACCCCATATCCATGCATCCCTGTATAATAAAGCATCCAG
         1690      1700      1710      1720      1730      1740      1750      1760      1770      1780      1790      1800

CAAAGCCCTGGTACCATGTAAAAACTGTCCTGGTTCTTTCCAAGGTATAGAGCATAGCTCTGGCCAGGGGCCCGGAGAACAGCCTTGTCTATAGGAAGAGAATGAGGTT
         1810      1820      1830      1840      1850      1860      1870      1880      1890      1900      1910      1920

TCTGCCTGCAT
         1930
```

Fig. 3B

```
           A  P  E  L  L  G  G  P  S  V  F  L  F  P  P  K
GCCCTAGAGTGGCCTGCATCCAGGACAGGTCCCAGTCGGGACACATCTGCCTCCATCTCTTCCTCAGCACCTGAACTCCTGGGAGGACCGTCAGTCTTCCTCTTCCCCCAAAA
                                            HUIGG3-LA234  GC
                                            HUIGG3-LE235       GAA
                                            HUIGG3-LA235       GCA
                                            HUIGG3-GA236           CC
                                            HUIGG3-GA237           CC
1570      1580      1590      1600      1610      1620      1630      1640      1650      1660      1670      1680
                                                                              L234
                                                                              L235
                                                                              G236
                                                                              G237
         CH 2 Domain
 P  K  D  T  L  M  I  S  R  T  P  E  V  T  C  V  V  V  D  V  S  H  E  D  P  E  V  Q  F  K  W  Y  V  D  G  V  E  V  H  N
CCCAAGGATACCCTTATGATTTCCCGGACCCCTGAGGTCACGTGCGTGGTGGTGGACGTGAGCCACGAAGACCCCGAGGTCCAGTTCAAGTGGTACGTGGACGGCGTGGAGGTGCATAAT
1690      1700      1710      1720      1730      1740      1750      1760      1770      1780      1790      1800
```

Fig. 6

```
                                                            A   P   N
CCCTGTAATGGAGGATAAGCCATGTACAAATCCATTTCCATCTCTCCTCATCAGCTCCTA

253
                                                               *
     L  E  G  G  P  S  V  F  I  F  P  P  N  I  K  D  V  L  M  I
ACCTCGAGGGTGGACCATCCGTCTTCATCTTCCCTCCAAATATCAAGGATGTACTCATGA
                                                  3' ATGAGTACC

S  L  T  P  K  V  T  C  V  V  V  D  V  S  E  D  D  P  D  V
TCTCCCTGACACCCAAGGTCACGTGTGTGGTGGTGGATGTGAGCGAGGATGACCCAGACG
GGAGGGACT 5'  Ile253-Ala

Q  I  S  W  F  V  N  N  V  E  V  H  T  A  Q  T  Q  T  H  R
TCCAGATCAGCTGGTTTGTGAACAACGTGGAAGTACACACAGCTCAGACACAAACCCATA

297
        *
   E  D  Y  N  S  T  I  R  V  V  S  T  L  P  I  Q  H  Q  D  W
GAGAGGATTACAACAGTACTATCCGGGTGGTCAGCACCCTCCCCATCCAGCACCAGGACT
     3' TCCTAATGCGGTCATGAT 5' Asn297-Ala 318     320    322                                333
            *       *      *                                  *
     M  S  G  K  E  F  K  C  K  V  N  N  K  D  L  P  S  P  I  E
GGATGAGTGGCAAGGAGTTCAAATGCAAGGTCAACAACAAAGACCTCCCATCACCCATCG
          3' CACCGTTCCGGAAGT 5' Glu318-Ala              3' TGGGTAGC
              3' CCTCAAGCGGACGTTCC 5' Lys320-Ala
                   3' TTACGCGGCAGTTG 5' Lys322-Ala

337
     *
  R  T  I  S  K  I  K
AGAGAACCATCTCAAAAATTAAAGGTGGGACCTGCAGGACA
GGTCTT 5' Glu333-Ala
   3' GGTAGCGGTTTTAA 5' Ser337-Ala
```

*Fig. 7*

ANTIBODIES WITH ALTERED EFFECTOR FUNCTIONS

This is a continuation of application Ser. No. 08/208,084 filed Mar. 9, 1994, pending, which is a continuation of application Ser. No. 07/814,035, filed Dec. 24, 1991, abandoned, which is a continuation of application Ser. No. 07/303,668, filed Jan. 18, 1989, abandoned, the entire specifications of each of which are incorporated herein by reference.

FIELD OF INVENTION

This invention relates to altered antibodies and concerns an antibody with an altered effector function, a method of producing such an antibody, and a process for altering an effector function of an antibody.

BACKGROUND TO THE INVENTION

Antibodies, or immunoglobulins, comprise two heavy chains linked together by disulphide bonds and two light chains, each light chain being linked to a respective heavy chain by disulphide bonds. The general structure of an antibody of class IgG (ie an immunoglobulin (Ig) of class gamma (G)) is shown schematically in FIG. 1 of the accompanying drawings.

Each heavy chain has at one end a variable domain followed by a number of constant domains. Each light chain has a variable domain at one end and a constant domain at its other end, the light chain variable domain being aligned with the variable domain of the heavy chain and the light chain constant domain being aligned with the first constant domain of the heavy chain.

Antigen binds to antibodies via an antigen binding site in the variable domains of each pair of light and heavy chains. Other molecules, known as effector molecules, bind to other sites in the remainder of the molecule, ie other than the antigen binding sites, and this portion of antibody will be referred to herein as "the constant portion" of an antibody, such sites being located particularly in the Fc region constituted by the portions of the heavy chains extending beyond the ends of the light chains.

Antibodies have several effector functions mediated by binding of effector molecules. For example, binding of the C1 component of complement to antibodies activates the complement system. Activation of complement is important in the opsonisation and lysis of cell pathogens. The activation of complement also stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Although various Fc receptors and receptor sites have been studied to a certain extent, there is still much which is unknown about their location, structure and functioning.

SUMMARY OF THE INVENTION

According to one aspect of the present invention, there is provided a modified antibody of the class IgG in which at least one amino acid residue in the constant portion (as herein defined) has been replaced by a different residue, altering an effector function of the antibody as compared with unmodified antibody.

An effector function of an antibody may be altered by altering, ie enhancing or reducing, the affinity of the antibody for an effector molecule such as an Fc receptor or a complement component. Binding affinity will generally be varied by modifying the effector molecule binding site, and in this case it is appropriate to locate the site of interest and modify at least part of the site in a suitable way. It is also envisaged that an alteration in the binding site on the antibody for the effector molecule need not alter significantly the overall binding affinity but may alter the geometry of the interaction rendering the effector mechanism ineffective as in non-productive binding. It is further envisaged that an effector function may also be altered by modifying a site not directly involved in effector molecule binding, but otherwise involved in performance of the effector function.

By altering an effector function of an antibody it may be possible to control various aspects of the immune response, eg enhancing or supressing various reactions of the immune system, with possible beneficial effects in diagnosis and therapy.

For example, it is known to use monoclonal antibodies for guided localisation of malignant lesions in patients with a number of solid tumours, such as ovarian and testicular cancer. However, their general use has been limited because several major problems such as false positive, false negative as well as non-specific localisation continue to exist. The amounts of radioiodine-labelled tumour-associated monoclonal antibody reaching their target tissues after intravenous administration in humans are small (Epenetos et al, 1986). One problem is a high non-specific uptake in normal lymph nodes and the rapid catabolism of murine monoclonal antibodies in these studies. The use of human monoclonal antibodies may also give high backgrounds due to non-specific binding to the high affinity receptors (Fc gamma RI) of the lymphatics, liver and spleen. An altered monoclonal antibody which does not bind to this high affinity receptor may improve antibody-guided tumour localisation by enhancing specific turnout uptake of the antibody while decreasing the background due to non-specific binding to FcR.

Ideally, monoclonal antibodies used for therapy of tumours would be radiolabelled or exploit the host's own effector mechanisms. It is not yet clear which of these will be the most significant in vivo for clearance of antibody-coated target cells, but ADCC by mononuclear cells, particularly K cells, seems the most effective (Hale et al, 1985). It may be possible to produce antibodies which react only with certain types of Fc receptor; for example, modified antibodies could be produced which do not bind the high afinity Fc gamma RI of cells of the R.E.S. but, when aggregated on a surface may bind Fc gamma RII expressing cells and trigger ADCC and specifically destroy, the target cell.

Production of a modified antibody can be carried out by any suitable technique including techniques that are well known to those skilled in the art. For example an appropriate protein sequence, eg forming part or all of a relevant constant domain, eg $C_H2$ domain, of an antibody, and include appropriately altered residue(s) can be synthesised and then chemically joined into the appropriate place in an antibody molecule.

Preferably, however, genetic engineering techniques are used for producing an altered antibody. The presently preferred such technique comprises:

a) preparing a first replicable expression vector including a suitable promoter operably linked to a DNA sequence which encodes at least part of an IgG heavy or light chain, eg the $V_H$, $C_H1$ and $C_H2$ domains of an IgG heavy chain, the appropriate residue(s) of which have been altered;

b) if necessary, preparing a second replicable expression vector including a suitable promoter operably linked to a DNA sequence which encodes a complementary Ig light or heavy chain;

c) transforming a cell line with the first or both prepared vectors; and d) culturing said transformed cell line to produce an altered antibody.

The present invention also includes vectors used to transform the cell line, vectors used in producing the transforming vectors, cell lines transformed with the transforming vectors, cell lines transformed with preparative vectors, and methods for their production.

Preferably, the cell line which is transformed to produce the antibody of altered effector function is an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof.

Although the cell line used to produce the antibody of altered effector function is preferably a mammalian cell line, any other suitable cell line, such as a bacterial cell line or a yeast cell line, may alternatively be used. In particular, it is envisaged that *E. coli*-derived bacterial strains could be used.

It is known that some immortalised lymphoid cell lines, such as myeloma cell lines, in their normal state secrete isolated Ig light chains. If such a cell line is transformed with the vector prepared in step a) of the process defined above, it will not be necessary to carry out step b) of the process, provided that the normally secreted chain is complementary to the chain encoded by the vector prepared in step a).

However, where the immortalised cell line does not secrete on does not secrete a complementary chain, it will be necessary to carry out step b). This step may be carried out by further manipulating the vector produced in step a) so that this vector encodes not only the heavy chain but also the light chain. Alternatively, step b) is carried out by preparing a second vector which is used to transform the immortalised cell line.

The techniques by which such vectors can be produced and used to transform the immortalised cell lines are well known in the art, and do not form any part of the invention.

In the case where the immortalised cell line secretes a complementary light chain, the transformed cell line may be produced, for example, by transforming a suitable bacterial cell with the vector and then fusing the bacterial cell with the immortalised cell line by spheroplast fusion. Alternatively, the DNA may be directly introduced into the immortalised cell line by electroporation.

The DNA sequence encoding the relevant altered portion of the antibody may be prepared by oligonucleotide synthesis. Alternatively, the DNA encoding the altered portion may be prepared by primer directed oligonucleotide site-directed mutagenesis. This technique in essence involves hybridising an oligonucleotide coding for a desired mutation with a single strand of DNA containing the mutation point and using the single strand as a template for extension of the oligonucleotide to produce a strand containing the mutation. This technique, in various forms, is described by Zoller and Smith, 1982; Zoller and Smith, 1984; Norris et al., 1983; Kramer et al., 1982.

For various reasons, this technique in its simplest form does not always produce a high frequency of mutation. An improved technique for introducing both single and multiple mutations in an M13 based vector has been described by Carter et al., 1985a.

The invention can be applied to antibodies of different species, eg human, rodent (mouse, rat, hamster) etc, and different class. The invention can also be applied to naturally occuring antibodies, chimeric antibodies (eg of the type disclosed in PCT/GB85/00392) or altered antibodies altered in other ways (eg of the type disclosed in GB 2188638).

As one example, work has been carried out on IgG, to alter the binding affinity for the receptor known as Fc gamma R1.

In man, and in mouse, three Fc gamma receptors have been partially characterised: Fc gamma R1, Fc gamma RII, and FC gamma $R_{lo}$, and these are expressed on distinct but overlapping haematopoetic cell types (Anderson and Looney, 1986). Furthermore, these different receptors have differing affinities for IgG subclasses. As mentioned above, binding of antibody to these receptors on cell surfaces triggers a number of important and diverse biological responses. It is not known which receptor, if any, is primarily responsible for which effect, but evidence suggests that it is the low affinity receptors which are relevant for these physiological effects. The receptors in man and mouse have been proposed as homologues on a number of physical criteria. Cloning and sequencing of the low affinity Fc gamma RII from both sources has confirmed this prediction (Lewis et al 1986, Ravetch et al 1986). The high affinity receptor Fc gamma R1 has been studied extensively and in both man and mouse binds monomeric IgG (man=IgG1 and IgG3; mouse=IgG2a) and is found on the same cell types.

The Fc region of IgG comprises two constant domains, $C_H2$ and $C_H3$, as shown in FIG. 1. As with the mouse system much effort has gone into the determination of the contribution of each of the two domains, C gamma 2 and C gamma 3, to the interaction. Isolated $C_H3$ domains, (pFc' fragments) were reported to have no inhibitory activity on the formation of monocyte rosettes (Abramson et al 1970). But other reports have shown that this fragment was capable of inhibiting Fc gamma R1 binding (Barnett-Foster et al 1980) indicating that the C gamma 3 domain was involved in binding human Fc gamma R1. This view became predominant until Woof and colleagues demonstrated that this inhibitory activity could be removed by extensive purification of the pFc' fraction by passage over protein A and anti-L chain columns. These purified samples showed no inhibition of monomer binding (Woof et al 1984). Additionally, the ability of monoclonal antibodies directed again epitopes on the $C_H3$ domain to interact with FcR bound antibody, but not those to epitopes on $C_H2$, is consistent with a binding site on the $C_H2$ domain (Partridge et al, 1986).

In a comprehensive study of the high affinity receptor for human IgG on human monocytes (Fc gamma R1) Woof, Burton and colleagues also localised the binding-site to the $C_H2$ domain of human IgG1 (Woof et al, 1984; Partridge et al, 1986). A range of IgG subclasses from different species, as well as fragments of human immunoglobulin, were tested for their ability to inhibit the interaction between human IgG and human monocytes in a direct-binding microassay.

IgGs were grouped into those found to exhibit tight, intermediate or weak binding to the FcR on human monocytes (Fc gamma R1). By comparison of the amino-acid sequences in these different affinity groups a potential monocyte-binding site in the hinge-link region (Leu234 -Ser239) was proposed, with possible involvement of the two beta-strands and joining bend formed by the residues Gly316-Lys338 (Woof et al, 1986). The latter region had already been proposed as the Clq binding site (Burton et al, 1980). The human Fc gamma R1 receptor binds human IgG1 and mouse IgG2a as a monomer, but the binding of mouse IgG2b is 100-fold weaker (Woof et al, 1986). A comparison of the sequence of these proteins in the hinge-link region shows that the sequence (234 to 238) Leu-Leu-Gly-Gly-Pro in the strong binders becomes Leu-Glu-Gly-Gly-Pro in mouse gamma 2b.

In an attempt to alter the binding affinity the substitution Glu235 by Leu was made in the mouse IgG2b heavy chain. The numbering of the residues in the heavy chain is that of the EU index (see Kabat et al., 1983). The normal mouse antibody does not bind to human Fc gamma R1, but by changing residue 235 from glutamic acid to leucine, eg by site directed mutagenesis, affinity for the human Fc gamma R1 is increased by over 100-fold. The magnitude of the increase in affinity was much greater than could have been expected and suggests that single amino acid changes in this region could be used to produce altered antibodies more suited to a range of in vivo applications in man and other animals. This change does not alter other Ig binding sites such as for complement component Clq.

It should also be possible to alter the affinity of Fc gamma R1 binding by replacing the specified residue with a residue having art inappropriate functionality on its sidechain, or by introducing a charged functional group, such as Glu or Asp, or perhaps an aromatic non-polar residue such as Phe, Tyr or Trp.

These changes would be expected to apply equally to the murine, human and rat systems given the seuqence homology between the different immunoglobulins. It has been shown that in human IgG3, which binds to the human Fc gamma R1 receptor, changing Leu 235 to Glu destroys the interaction, of the mutant for the receptor. The binding site for this receptor can thus be switched on or switched off.

Mutations on adjacent or close sites in the hinge link region (eg replacing residues 234, 236 or 237 by Ala) indicate that alterations in residues 234, 235, 236 and 237 at least affect affinity for the Fc gamma R1 receptor.

Hence in a further aspect of the present invention provides a modified antibody of the class IgG having an altered Fc region with altered binding affinity for Fc gamma R1 as compared with the unmodified antibody.

Such an antibody conveniently has a modification at residue 234, 235, 236 or 237.

Affinity for other Fc receptors can be altered by a similar approach, for controlling the immune response in different ways.

As a further example, work has also been called out to alter the lytic properties of Ig following binding of the Cl component of complement.

The first component of the complement system, Cl, actually comprises three proteins known as Clq, Clr and Cls which bind tightly together. It has been shown that Clq is responsible for binding the three protein complex to Ig.

It has been shown that isolated Fc fragment inhibits the interaction of Clq with an Ig (Yasmeen eg al., 1976).

It has also been shown that the binding of Clq is dependent on ionic strength, suggesting that ionic interactions are involved.

It is possible to cleave the $C_H3$ domain from the remainder of an Ig molecule, and it has been shown that deletion of the $C_H3$ domain does not abolish Clq binding activity (Colomb and Porter, 1975).

It is also possible to isolate the $C_H2$ domain from Igs. It has been shown that such isolated $C_H2$ domains have the same binding affinity for Clq as do isolated Fc fragments (Isenman et al., 1975).

From this, it has been inferred that the binding site for Clq is located in the $C_H2$ domain of the Ig. Various attempts have been made to identify the particular amino acid residues in the $C_H2$ domain involved in Clq binding. In a first approach, synthetic peptides corresponding to short sections of the $C_H2$ domain were tested for inhibition of Clq binding. This identified two possible binding sites (Boakle et al., 1975 and Lukas et al., 1981).

In a second approach, a comparison of the sequences of several Ig $C_H2$ domains was made in conjunction with studies of their three dimensional structure. This led to the identification of two further proposals for the site of Clq binding (Brunhouse and Cebra, 1979 and Burton et al., 1980).

It has now been found that the Clq binding activity of an antibody can be altered by providing the antibody with an altered $C_H2$ domain in which at least one of the amino acid residues 318, 320 and 322 of the heavy chain has been changed to a residue having a different side chain.

The numbering of the residues in the heavy chain is that of the EU index (see Kabat et al., 1983).

The present inventors have discovered that, in a specific Clq-binding Ig referred to below, by changing any one of residues 318 (Glu), 320 (Lys) and 322 (Lys), to Ala, it is possible to abolish Clq binding.

Moreover, by making mutations at these residues, it has been shown that Clq binding is retained as long as residue 318 has a hydrogen-bonding side chain and residues 320 and 322 both have a positively charged side chain.

The Applicants believe that these three residues are probably involved directly in the binding Clq to IgG. However, it is also possible that these residues are not directly involved in physical contact with Clq. These residues may help one $C_H2$ domain to pack against an adjacent domain in an IgG agregate, thus producing the at least two molecules of IgG together which are required for Clq binding. If this is the case, the Clq may be in direct contact with the IgG in an entirely different area. The Applicants, however, do not wish to be in any way limited to either of these theories.

Altering residue 333 (Glu), which is close to the three specified residues, or residue 253 (Ile), which is distant from the three specified residues, does not alter Clq binding activity, even though previous studies have implicated residue 333 (Glu) in Clq binding.

It is to be noted that residues 318, 320 and 322 are highly conserved in mouse and human IgGs which are complement binding.

It has also been shown that alteration of the three specified residues only alters the Clq binding activity, and does not alter antigen binding-activity, protein A binding activity (protein A binds to the $C_H2/C_H3$) interface), or the ability of the Fc to bind to mouse macrophages.

It is believed that the process of the present invention can be used to abolish C1q binding activity by replacing any one of the three specified residues with a residue having an inappropriate functionality on its side chain. It is not necessary to replace the ionic residues only with Ala to abolish C1q binding. It will also be possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. It will also be possible to use such polar non-ionic residues as Ser, Thr, Cys, and Met in place of residues 320 and 322, but not 318, in order to abolish C1q binding activity.

It may be that the side chains on ionic or non-ionic polar residues will be able to form hydrogen bonds in a similar manner to the bonds formed by the Glu residue. Therefore, replacement of the 318 (Glu) residue by a polar residue may modify but not abolish C1q binding activity.

It has further been shown that replacing residue 297 (Asn) with Ala results in removal of lytic activity while only slightly reducing (about three fold weaker) affinity for C1q. It is thought this is because the alteration destroys the glycosylation site and that the presence of carbohydrate is required for complement activition. Any other substitution at this site will also destroy the glycosylation site.

Further, the mutation Lys 320 to Gln has an affinity for C1q only slightly weaker than the wild type but is non lytic. This indicates that good C1q binding may be insufficient for lysis and that perhaps a precise orientation of C1q is required.

All antibody isotypes sequenced to date possess the C1q binding motif, or a closely related motif which is effective in binding C1q when it is transplanted into the mouse IgG2b antibody. Clearly there must be further determinants for lysis. For example, antibody isotypes with short hinges and low segmental flexibility are non-lytic (Oi et al. 1984) suggesting that (a) the interaction of C1q with the motif may be sterically blocked due to close approach of the Fc by the Fab arms (Leatherbarrow et al., 1985) or (b) the interaction of C1q and antibody requires an exact alignment for lysis and therefore requires some flexibility per se.

The present invention is now described, by way of example only, with reference to the accompanying drawings, in which:

FIG. 3A and FIG. 3B show the sequence of mouse IgG gamma 2b gene;

FIG. 6 shows the nucleotide sequence and protein sequence of the human gamma 3 gene; and FIG. 7 shows the nucleotide sequence encoding the $C_H2$ domain of mouse IgG2b anitbody with mutants and the sequences of the oligonucleotides used to construct some of the mutants referred to below.

The following concerns experiments on mouse IgG2b to alter the affinity thereof for human Fc gamma R1.

DNA encoding the variable and constant region exons of antibodies can be manipulated in vitro and reintroduced into lymphoid cell lines (Neuberger, 1985). Using vectors based on pSV-gpt (Mulligan & Berg 1981) and the Ig heavy chain promotor/enhancer, antibodies can be expressed and secreted. One such vector, pSV-VNP 2b (Neuberger and Williams 1985) encodes a variable domain which binds nitrophenylacetyl (NP) and the constant domains of the natural mouse IgG2b antibody. The antibody produced using this vector does not bind to human Fc gamma R1.

Figure 1:
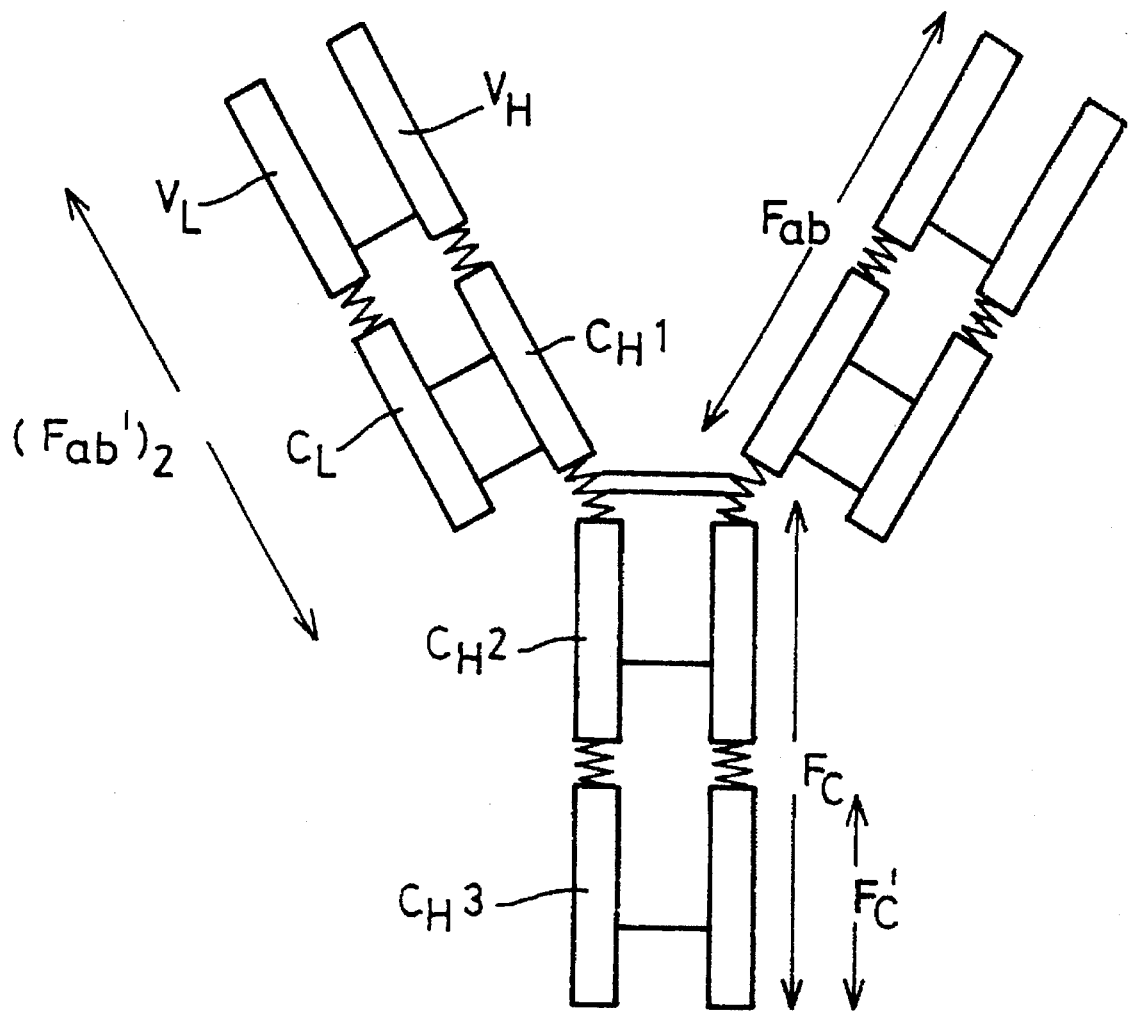
FIG. 1 illustrates the structure of an Ig.
Figure 2:
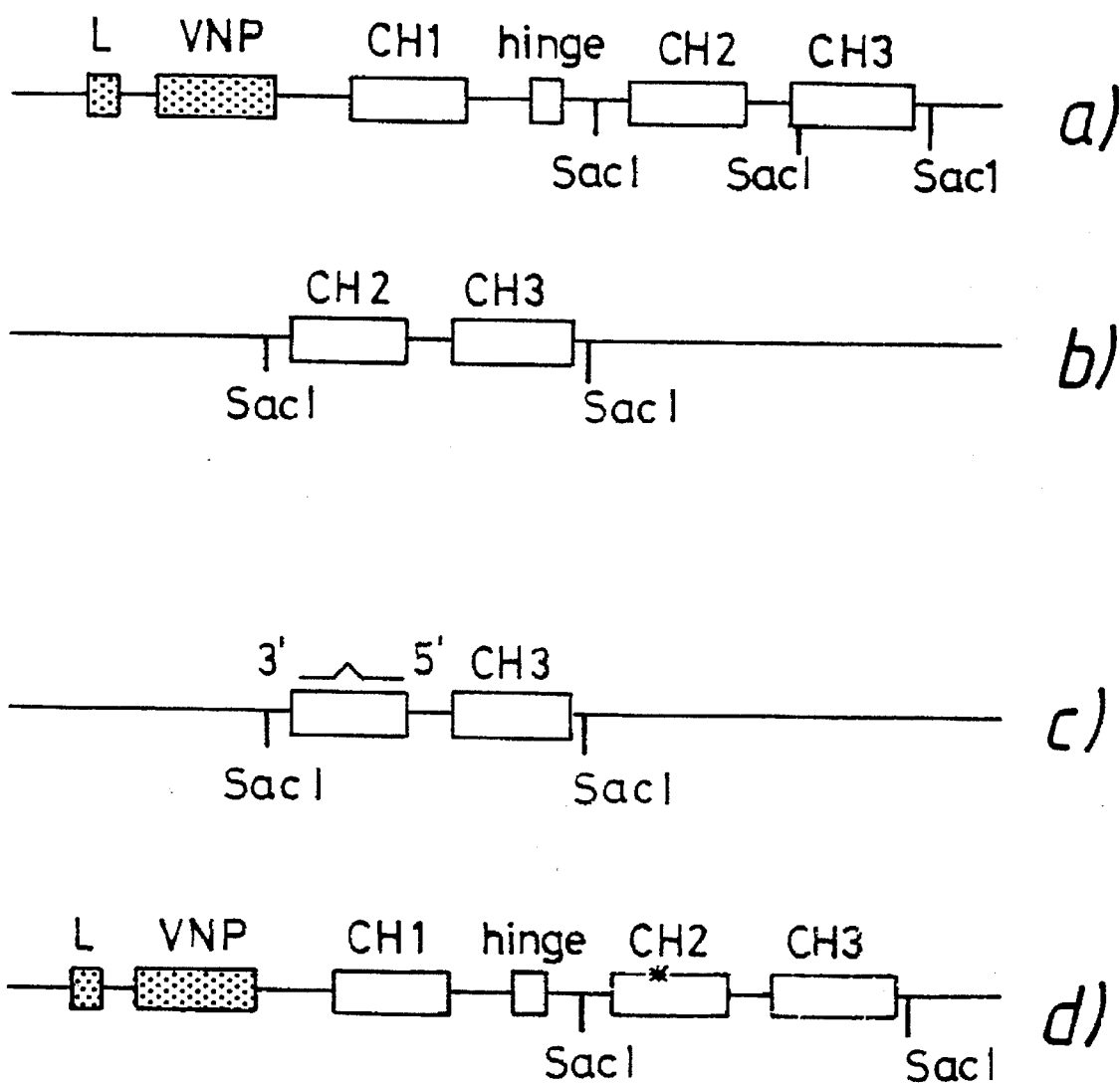
FIG. 2 illustrates the sequence of cloning steps used to produce an antibody of altered Fc gamma R1 binding activity.

Part of the structure of the pSV-VNP 2b vector is shown in FIG. 2(a). The vector was partially digested with SacI and a fragment containing both the $C_H2$ and $C_H3$ domains was cloned into plasmid M13K19 (Carter et al. 1985a) as shown in FIG. 2(b).

The SacI site at the N-terminal end of the $C_H3$ domain was removed by site directed mutagenesis with an oligonucleotide which retains the amino acid sequence at this N-terminal end.

A point mutation in the $C_H2$ domain was then produced using a synthetic oligonucleotide as shown in FIG. 3, in the region indicated between bases 956 and 975 and marked EL235. Further details of the construction of the mutation is given below. The mechanism of the point mutation is shown in FIG. 2(c).

The mutant $C_H2$-$C_H3$ fragments were recloned into the pSV-VNP 2b vector to replace the wild type $C_H2$-$C_H3$ domains. The mutant pSV-VNP 2 b vectors were incorporated into J558L, cultured to produce antibody and the antibody mutant known as EL235 was purified on NIP-Sepharose.

Construction of mutations in the C gamma 2 exon

Mutations were constructed in the M13B19-C gamma 2/C gamma 3 as in Carter et al (1985a). The principles and methods are described in detail in Carter et al, (1985b), and Duncan.

Figure 4:
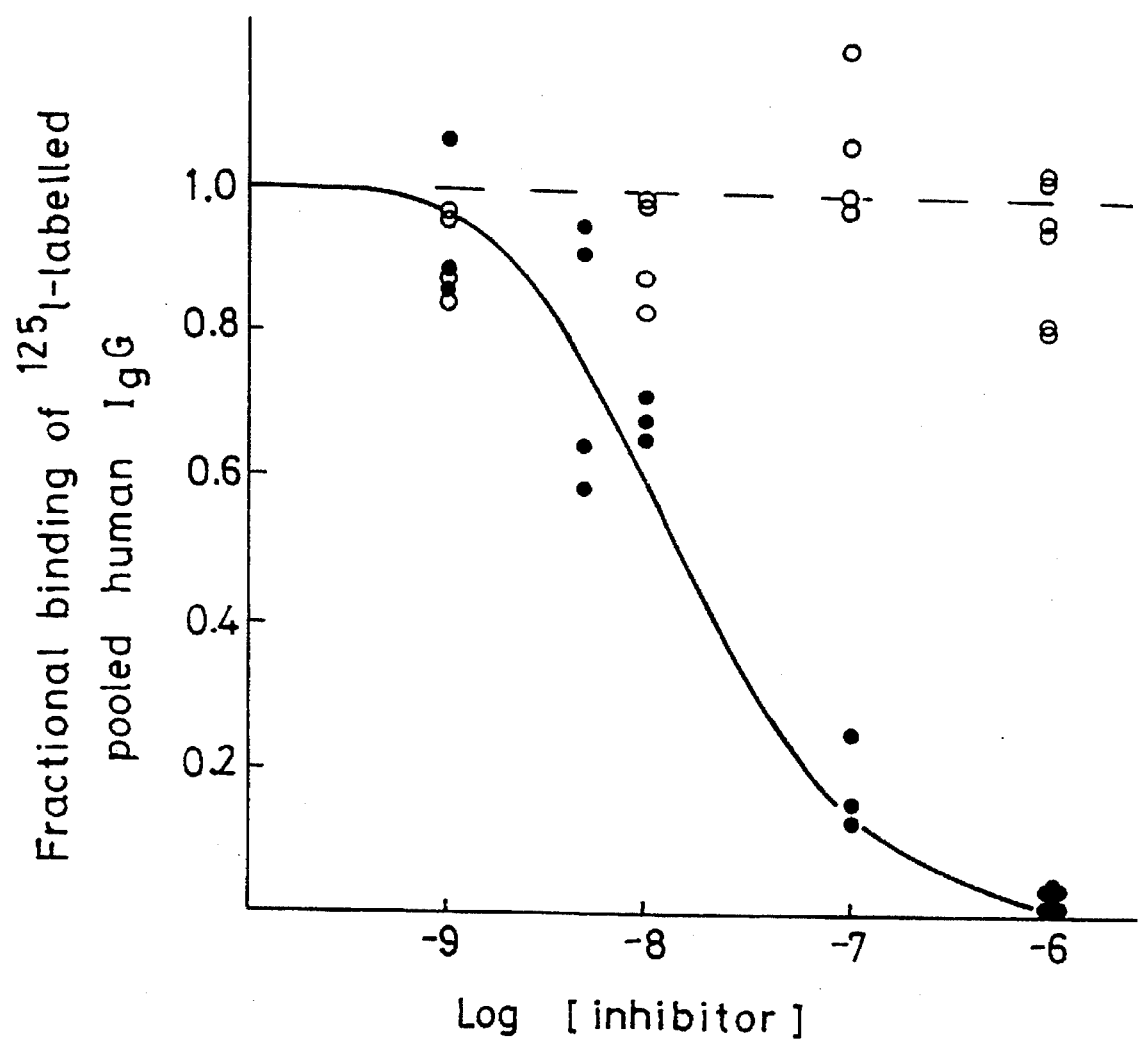
FIG. 4 is a graph illustrating inhibition of $^{125}$I-labelled pooled human IgG binding to high affinity receptors on U937 cells by mouse gamma 2b immunoglobulins.

The mutant EL235 was assayed by inhibition of binding of human IgG as well as by direct binding to a human monocyte cell line (Woof et al, 1984; 1986). Inhibition of binding of monomeric $^{125}$I-labelled normal pooled human IgG to high affinity Fc receptors on a human monocyte cell line, U937, was measured in a quantitative microassay system in which free and cell-bound label were separated by centrifugation through a water-immiscible oil. The binding of wild-type gamma 2b and the mutant EL235 were compared by competition of labelled polyclonal human IgG. FIG. 4 shows the inhibition curves for this experiment. In FIG. 4 empty circles represent wild type and solid circles mutant EL235. The result has been normalised such that the fractional binding of $^{125}$I-IgG=1 in the absence of inhibitors. The mutant inhibits the binding of human IgG1; the wild type protein showed no inhibitory activity. Direct binding of radiolabelled mutant EL235 to U937 cells gives a binding constant of $3.13 \times 10^8$ $M^{-1}$ (FIG. 5), very similar to the value for pooled human IgG in the same experiment.

Figure 5:
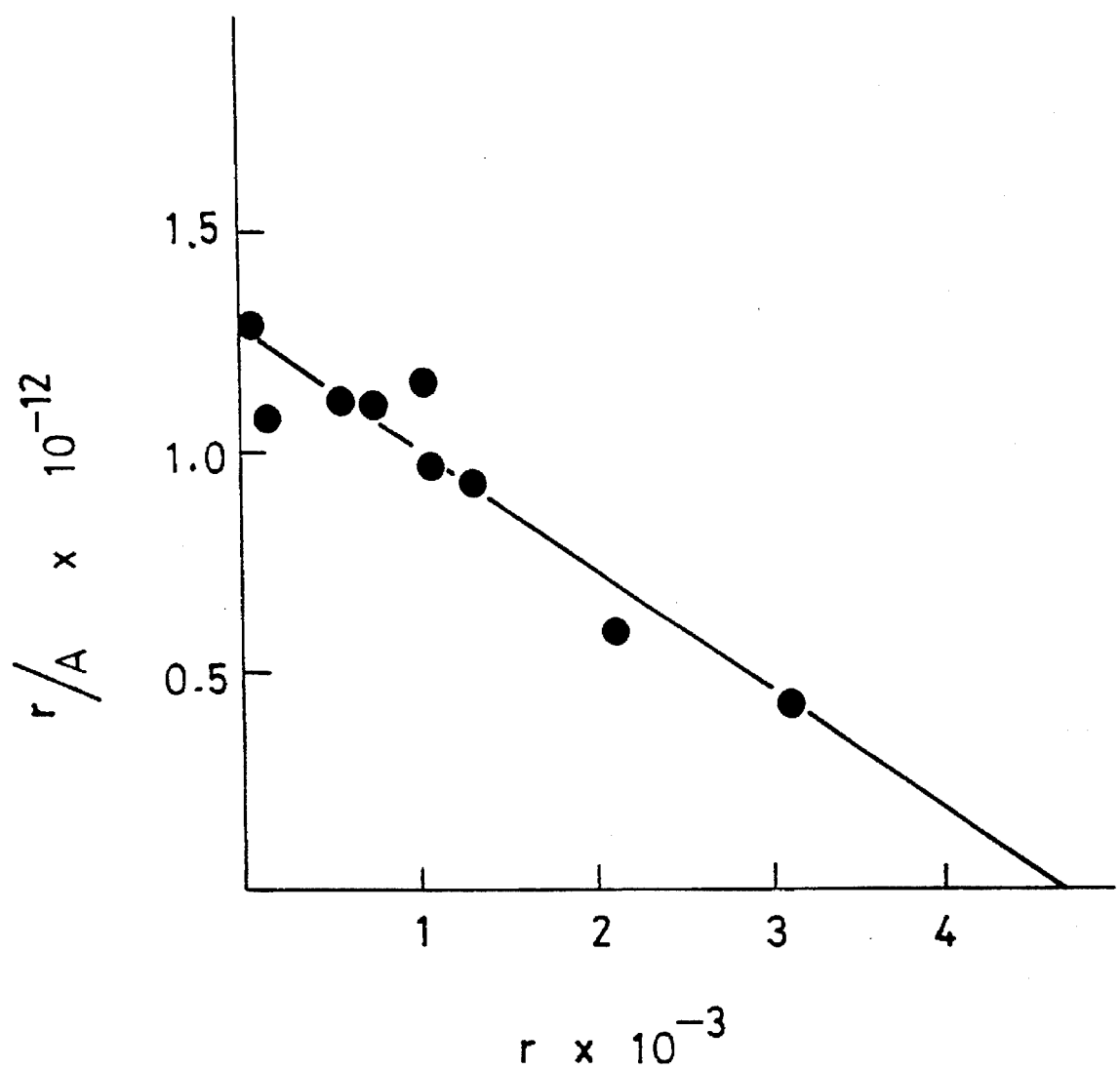
FIG. 5 is a Scatchard plot of $^{125}$I-EL235 binding to U937 high affinity receptors.

FIG. 5 is a typical Scatchard plot of $^{125}$I-EL235 binding to U937 high affinity FC receptors. The number of moles of $^{125}$I-EL235 bound per mole of cells, r, was calculated using the following relationship:

$$r = \frac{6 \times 10^{23} \times IgG2b}{\text{no. cells}/L}$$

where IgG2b is the concentration of bound $^{125}$I-EL235. A represents the concentration of free $^{125}$I-EL235. The coefficient of correlation of the plot was 0.95.

Thus a point mutation altered the binding affinity of mouse IgG2b for human Fc gamma R1 by greater than 100-fold.

Mutations were made in the human gamma 3 gene (Huck et al., 1985); the Hind III-SpHI fragment was first subcloned into M13 mp19 after attaching BamHI linkers. Then sythetic oligonucleotides were used as described previously to make the mutations:

| |
|---|
| 234 Leu to Ala |
| 235 Leu to Glu |
| 236 Gly to Ala |
| 237 Gly to Ala | as indicated on FIG. 6.

The BamHI fragment was attached to a Hind III-BamHI fragment encoding the variable domain of the B18 antibody (as in Neuberger et al., 1984 and 1985) and cloned for expression into a pSVgpt vector.

The properties of the recombinant antibodies in binding in Fc gamma R1 were determined indirectly in a competition assay as described in connection with FIG. 4. Table 1 shows the concentration of antibody required to inhibit the binding of $^{125}$I labelled pooled human IgG to U937 cells.

TABLE 1

| | $I_{50}$ (M) |
|---|---|
| Wild type (Leu 234, Leu 235, Gly 236, Gly 237) | $10^{-8}$ |
| Mutants | |
| Ala 234 | $4 \times 10^{-8}$ |
| Glu 235 | greater than $10^{-6}$ |
| Ala 236 | $3 \times 10^{-8}$ |
| Ala 237 | $3 \times 10^{-7}$ |

The table gives the approximate values of $I_{50}$ (ie the concentration of IgG3 at which the fractional binding of $^{125}$I labelled pooled human IgG is 0.5).

These findings have important implications for the use of antibodies, both murine and human, in diagnostics and therapy, as discussed above.

The present results show that Fc gamma R1 receptor can be selectively switched on or off, and this might be of great use in the preparation of antibodies for in vivo diagnosis or therapy of humans as well as other animals.

Similar experiments were carried out at mouse lgG2b to alter lytic activity following binding of C1q. Further mutants of the pSV-VNP 2b vector were produced using the procedure described above, with point mutations being produced in the $C_H2$ domain using synthetic oligonucleotides as shown in FIG. 7, and antibodies produced as previously described.

Antibody produced using the pSV-VNP 2b vector, with wild type $C_H2$-$C_H3$ domains binds C1q (see Table 2).

The ability of the resulting purified antibodies to lyse specifically NIP-kephalin derivatised sheep red blood cells (Weltzien et al., 1984) was tested in a quantitative haemolysis microassay (Young et al., 1986). The results of the test are shown in Table 2. The titre in ug/ml antibody represents the amount of antibody required for 50% lysis after 30 minutes at 37° C.

A number of the mutant antibodies were tested for affinity for radiolablled C1q (Leatherbarrow and Dwek, 1984) after aggregating the anti-NP antibodies on NP-Affigel. The results are shown also in Table 2.

TABLE 2

| IgG | titre (ug/ml) | Affinity nM |
|---|---|---|
| MoIgG2b | 3 | 10 |
| MoIgM | 0.15 | — |
| MoIgG1 | x | — |
| Pro 331 - Ala | 3 | — |
| Pro 331 - Gly | — | 12 |
| Glu 333 - Ala | 3 | 12 |
| Thr 335 - Ala | 3 | 10 |
| Ser 337 - Ala | 3 | 11 |
| Glu 283 - Ala | 3 | — |
| His 285 - Ala | 3 | 12 |
| His 290 - Ala | 3 | 11 |
| Glu 294 - Ala | 3 | — |
| Glu 235 - Ala | 3 | — |
| Lys 248 - Ala | 3 | — |
| Ile 253 - Ala | 3 | 9 |
| Ser 267 - Ala | 3 | — |
| Asp 270 - Ala | 3 | — |
| Gln 274 - Ala | 3 | — |
| Lys 317 - Ala | 3 | — |
| Lys 236 - Ala | 3 | — |
| Lys 340 - Ala | 3 | — |

Mutations of MoIgG2b which abolish lytic activity

| | | |
|---|---|---|
| Glu 318 - Val | x | — |
| Glu 318 - Ala | x | greater than 300 |
| Lys 320 - Ala | x | greater than 300 |
| Lys 320 - Gln | x | 13 |
| Lys 322 - Ala | x | greater than 300 |
| Lys 322 - Gln | x | — |
| Asn 297 - Ala | x | 31 |

Mutations of MoIgG2b which conserve lytic activity

| | | |
|---|---|---|
| Glu 318 - Thr | 3 | 12 |
| Lys 320 - Arg | 3 | 11 |
| Lys 322 - Arg | 3 | 11 |

Antibodies with the $V_{NP}$ domain attached to human IgG1 and mouse IgG1 were kindly supplied by Dr M Bruggemann and Mr P T Jones respectively.

Mutants Glu318-Ala, Lys320-Ala and Lys322-Ala have a dramatically reduced affinity (Table 2). However, they retain binding for the NP hapten and protein A (which binds at the $C_H2$-$C_H3$ interface). This suggests that the loss of C1q binding is not due to major structural change in the antibody. Mutations in adjacent residues (Glu333-Ala) or distant residues (Ile253-Ala) retain C1q affinity.

The results suggest that a surface patch defined by the side chains of residues 318, 320 and 322 determine whether an IgG will interact with C1q. These residues are highly conserved in human and mouse IgGs, indicating that alterations of side chains at these three locations can be used to construct therapeutically useful variants of human $C_H2$ domains which do not activate complement, or which have an enhanced affinity for complement.

Evidence that this surface patch is the complete binding site for C1q comes from a polypeptide mimic containing the Glu X Lys X Lys motif which proved to inhibit C1q lysis in a model system. This work is described in a copending PCT application No. PCT/GB88/00213 of Research Corporation entitled "Complement Binding Peptide" filed on the same date as this application.

It will be appreciated that the present invention has been described above purely by way of illustration and that variations and modifications can be made without departing from the scope of the invention.

REFERENCES

Abramson, N., Gelfand, E. W., Jandl, J. H., and Rosen, F. S. (1970) J. Exp. Med. 132, 1207.

Anderson, C. L., and Looney R. J. (1986) Immunol. Today, 7, 264.

Barnett-Foster, D. E., Dorrington, K. J., and Painter, R. H. (1980) J. Immunol. 124, 2186

Boakle et al., (1975) Nature, 282, 742–743

Brunhouse and Cebra, (1979) Molec. Immun., 16, 907–917.

Burton et al., (1980) Nature, 288, 338–344.

Burton, D. R. (1985) Molec. Immunol. 22, 161.

Burton, D. R., Boyd, J., Brampton, A., Easterbrook-Smith, S., Emanuel, E. J., Novotny, J., Rademacher, T. W., van Schravendijk, R., Sternberg, M. J. E., and Dwet, R. A. (1980) Nature 288, 338.

Carter, P., Bedouelle, H., and Winter, G. (1985a) Nucleic Acids Res. 13, 4431–4443.

Carter, P., Bedouelle, H., Waye, M. Y., and Winter, G. (1985b) In: Oligonucleotide-site-directed mutagenesis in M13. Anglian Biotechnology Limited, Colchester, England.

Colomb and Porter (1975) Biochem J., 145, 177–183.

Duncan A. R., University of Cambridge Phd Thesis (to be published).

Epenetos, A., Shook, D., Durbin, H., Johnson, P., and Tayler-Papadimitriou, J. (1986) Cancer Res, 46,3183.

Hale, G., Clark, M., and Waldmann, H. (1985) J. Immunol. 1134, 3056.

Hale, G., and Waldmann, H. (1985) in Hybridoma Technology in the Biosciences and Medicine. T. Springer, ed. Plenum Press, New York.

Huber, H., and Fudenberg, H. H. (1968) Int. Arch. Allergy Appl. Immunol. 34, 18.

Huck et al., (1985) Nuc. Acids Res 14, 1779–1788.

Isenman et al., (1975) J. Immun., 114, 1726–1729.

Kabat et al., (1983) "Sequences of Proteins of Immunological Interest", US Dept. Health and Human Services.

Kalofonos, H. P., and Epenetos, A. (1986) Cancer Treatment Renews 13,243.

Kramer et al., (1982) Nuc. Acides Res., 10, 6475–6485.

Leatherbarrow and Dweck (1984) Molec Immun., 21, 321–327.

Leatherbarrow, R. J., Rademacher, T. W., Dwek, R. A., Woof, J. M., Clark, A., Burton, D. R., Richardson, N., and Feinstein, A. (1985) Molec, Immun. 22,407–415.

Lewis, V. A., Koch, T., Plutner, H., and Mellman, I. (1986) Nature 324, 372.

Lukas et al., (1981) J. Immun., 127, 2555–2560.

Mulligan, R. C., and Berg, P. (1981) Proc. Natl. Acad. Sci. USA 78,2072.

Neuberger, M. S., and Williams, G. T. (1986) Phil. Trans. R. Soc. Lond. A 317, 425–432.

Neuberger, M. S., Williams, G. T., Mitchell, E. B., Jouhal, S. S., Flanagan, J. G., and Rabbitts, T. H. (1985) Nature 314, 268.

Neuberger, M. S., Williams, G. T. and Fox, R. O. (1984) Nature, 312, 604–608

Norris et al., (1983) Nuc. Acids Res., 11, 5103–5112.

Oi, V. T., Minh-Vuong, T., Hardy, R. R., Reidler, J., Dangl, J. L., Herzenberg L. A. and Stryer (1984) Nature, 307, 136–140.

Partridge, L. J., Woof, J. M., Jefferis, R., and Burton, D. R. (1986) Molec. Immunol. 23, 1365.

Rayetch, J. V., Luster, A. D., Weinshank, R., Kochan, A., Pavlovec, D. A., Portnoy, J., Hulmes, J., Pan, Y. M. C., Unkeless, J. (1986) Science 234, 718.

Suggs, S. V., Hirose, T., Miyake, T., Kawashima, E. H., Johnson, M. J., Itakura, K., and Wallace, R. B. (1981) In: Developmental Biology using Purified Genes (D. Brown, ed.) Academic Press, New York.

Weltzien et al., (1984) Molec. Immunol., 21 801.

Woof, J. M., Jafaar, M. I., Jefferis, R., and Burton, D. R. (1984) Molec. Immun. 21, 523.

Woof, J. M., Partridge, L. J., Jefferis, R., and Burton D. R. (1986) Molec. Immun. 23, 319.

Yasmeen et al., (1976) J. Immun., 116, 518–522.

Young et al., (1986) Anal. Biochem., 154, 649–654.

Zoller and Smith (1982) Nuc. Acids Res., 10, 6487–650.

Zoller and Smith (1984) DNA, 3, 497–488.

We claim:

1. A modified antibody of class IgG, in which at least one amino acid from the heavy chain constant region selected from the group consisting of amino acid residues 234, 235, 236, 237, 297, 318, 320 and 322 is substituted with another amino acid which is different from that present in an unmodified antibody, thereby causing an alteration in an effector function while retaining binding to antigen as compared with the unmodified antibody.

2. The modified antibody according to claim 1, in which at least one amino acid from the heavy chain constant region selected from the group consisting of amino acid residues 234, 235, 236 and 237 is substituted with an amino acid which is different from that present in an unmodified antibody, thereby causing an alteration in binding affinity for a Fc receptor as compared with the unmodified antibody.

3. The modified antibody according to claim 2, having a reduced binding affinity for Fc gamma RI receptor as compared with unmodified antibody.

4. The modified antibody according to claim 2, wherein at least one amino acid from the heavy chain constant region selected from the group consisting of amino acid residues 234, 236 and 237 is substituted with alanine.

5. The modified antibody according to claim 2, wherein amino acid residue 235 from the heavy chain constant region is substituted with glutamine.

6. The modified antibody according to claim 1, in which amino acid residue 297 from the heavy chain constant region is substituted with an amino acid which is different from that present in an unmodified antibody, thereby causing a reduction in lytic properties as compared with the unmodified antibody.

7. The modified antibody according to claim 6, wherein amino acid 297 from the heavy chain constant region is substituted with alanine.

8. The modified antibody according to claim 1, in which at least one amino acid from the heavy chain constant region selected from the group consisting of amino acid residues 318, 320 and 322 is substituted with an amino acid which is different from that present in an unmodified antibody, thereby causing a reduction in binding affinity for Clq as compared with the unmodified antibody.

9. The modified antibody according to claim 8, wherein at least one amino acid from the heavy chain constant region selected from the group consisting of amino acid residues 318, 320 and 322 is substituted with alanine, thereby reducing C1q binding affinity.

10. The modified antibody according to claim 8, wherein amino acid residue 318 from the heavy chain constant region has been substituted with valine.

11. The modified antibody according to claim 8, wherein amino acid residue 322 from the heavy chain constant region is substituted with glutamine.

12. The modified antibody according to claim 1, comprising rodent or human IgG.

13. The modified antibody according to claim 1, wherein the unmodified antibody is a naturally occurring antibody, or a recombinantly altered antibody.

14. A process for modifying an antibody of class IgG, comprising substituting at least one amino acid from the heavy chain constant region selected from the group consisting of amino acid residues 234, 235, 236, 297, 318, 320 and 322 with an amino acid which is different from that present in an unmodified antibody, thereby altering an affinity for a effector molecule while retaining binding to antigen as compared with the affinity of the unmodified antibody.

15. A method of producing modified antibody of class IgG with an altered effector function as compared with unmodified antibody comprising:.
 (a) preparing a replicable expression vector comprising a suitable promoter operably linked to a DNA which encodes at least part of a constant region of an immunoglobulin heavy chain and in which at least one amino acid from the heavy chain constant region selected from the group consisting of amino acid residues 234, 235, 236, 237, 297, 318, 320 and 322 is substituted with an amino acid which is different from that present in an unmodified antibody thereby causing an alteration in an effector function while retaining binding to antigen as compared with the unmodified antibody;
 (b) transforming a cell line with said vector; and
 (c) culturing said transformed cell line to produce said modified antibody.

16. The method according to claim 15 further comprising after step (a):
 preparing a second replicable expression vector comprising a promoter operably linked to a DNA which encodes a complementary immunoglobulin light chain and wherein said cell line is further transformed with said vector.

17. The method according to claim 15, wherein the constant region of an immunoglobulin heavy chain has at least one amino acid selected from the group consisting of amino acid residues 234, 235, 236 and 237 substituted with an amino acid which is different from that present in an unmodified antibody, thereby causing an alteration in binding affinity for a Fc receptor as compared with the unmodified antibody.

18. The method according to claim 15, wherein said constant region of an immunoglobulin heavy chain has amino acid residue 297 substituted with an amino acid which is different from that present in an unmodified antibody, thereby causing a reduction in lytic properties as compared with the unmodified antibody.

19. The method according to claim 15, wherein said constant region of an immunoglobulin heavy chain has at least one amino acid selected from the group consisting of amino acid residues 318, 320 and 322 substituted with an amino acid which is different from that present in an unmodified antibody, thereby causing a reduction in binding affinity for C1q as compared with the unmodified antibody.

20. The method of claim 17, wherein at least one amino acid from the heavy chain constant region selected from the group consisting of amino acid residues 234, 236 and 237 is substituted with alanine.

21. The method of claim 17, wherein amino acid residue 235 from the heavy chain constant region is substituted with glutamine.

22. The method of claim 18, wherein amino acid 297 from the heavy chain constant region is substituted with alanine.

23. The method of claim 19, wherein at least one amino acid from the heavy chain constant region selected from the group consisting of amino acid residues 318, 320 and 322 is substituted with alanine, thereby reducing C1q binding affinity.

24. The method of claim 19, wherein amino acid residue 318 from the heavy chain constant region has been substituted with valine.

25. The method of claim 19, wherein amino acid residue 322 from the heavy chain constant region is substituted with glutamine.

* * * * *